United States Patent [19]

Minai et al.

[11] Patent Number: 4,957,867
[45] Date of Patent: Sep. 18, 1990

[54] PRODUCTION OF CYCLOPENTENONES BY ENZYME RESOLUTION

[75] Inventors: Masayoshi Minai, Moriyama; Yuji Ueda, Izumi; Takayuki Higashii, Kishiwada; Michitada Kondo, Kobe; Seiichi Kai, Nara, all of Japan

[73] Assignee: Sumitomo Chemical Company, Limited, Osaka, Japan

[21] Appl. No.: 55,362

[22] Filed: May 29, 1987

[30] Foreign Application Priority Data

| May 29, 1986 | [JP] | Japan | 61-125381 |
| Nov. 5, 1986 | [JP] | Japan | 61-263464 |
| Mar. 27, 1987 | [JP] | Japan | 62-075611 |
| Mar. 30, 1987 | [JP] | Japan | 62-079297 |

[51] Int. Cl.$^5$ .................. C12P 7/62; C12P 7/38
[52] U.S. Cl. ................... 435/280; 435/135; 435/136; 435/149
[58] Field of Search ............ 435/280, 135, 136, 149

[56] References Cited

U.S. PATENT DOCUMENTS

| 3,892,630 | 7/1975 | Kurozumi et al. | |
| 4,511,655 | 4/1985 | Minai et al. | 435/280 X |
| 4,607,013 | 8/1986 | Matsuda et al. | 435/280 |
| 4,729,953 | 3/1988 | Minai et al. | 435/280 |

FOREIGN PATENT DOCUMENTS

| 87107811 | 8/1989 | European Pat. Off. . |
| 61-92578 | 5/1986 | Japan . |

OTHER PUBLICATIONS

Miura et al, –Chem. Abst., vol. 89 (1978), pp. 105, 910n.
Chemical Abstracts, vol. 105, No. 19, Nov. 10, 1986, Abstract No. 170,652t.
Chemical Abstracts, vol. 102, No. 3, Jan. 21, 1985, Abstract No. 22,826a.
Chemical Abstracts, vol. 105, No. 19, Nov. 10, 1986, Abstract No. 168,493y.
Chemical Abstracts, vol. 105, No. 19, Nov. 10, 1986, Abstract No. 170,645t.
Chemical Abstracts, vol. 103, No. 15, Oct. 14, 1985, Abstract No. 121,764f.

*Primary Examiner*—Sam Rosen
*Attorney, Agent, or Firm*—Birch, Stewart, Kolasch & Birch

[57] ABSTRACT

A process for preparing an optically active cyclopentenone of the formula:

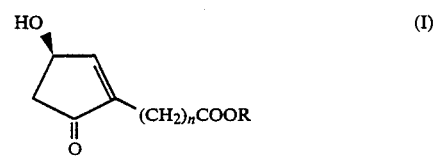

(I)

wherein R is a hydrogen atom or a lower alkyl group and n is an integer of 4 to 8, which comprises contacting a dl-cyclopentenone ester of the formula:

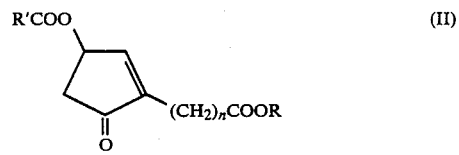

(II)

wherein R and n are each as defined above and R' is a lower alkyl group optionally substituted with halogen on an enzyme having a capability of hydrolyzing selectively either one of the d- or l-form isomer in the dl-cyclopentenone ester (II) in an aqueous medium for asymmetric hydrolysis.

37 Claims, No Drawings

PRODUCTION OF CYCLOPENTENONES BY ENZYME RESOLUTION

This invention relates to production of cyclopentenones. More particularly, it relates to a novel process for production of optically active cyclopentenones of the formula:

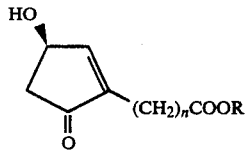

wherein R is a hydrogen atom or a lower alkyl group and n is an integer of 4 to 8.

Said optically active cyclopentenones (I) are useful as intermediates in the synthesis of agricultural chemicals, pharmaceuticals (e.g. prostaglandins), perfumes, etc.

For production of the cyclopentenones (I), there are known various processes, among which typical ones are set forth below.

(1) Tetrahedron Letters, 49, 4959 (1973)

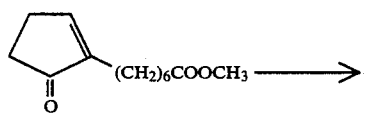

(2) J. Am. Chem. Soc., 97, 865 (1975)

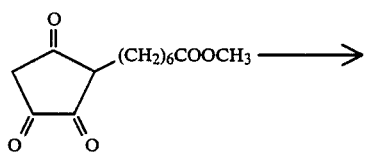

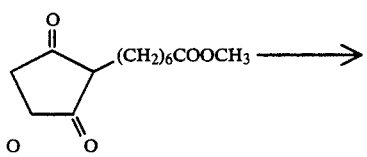

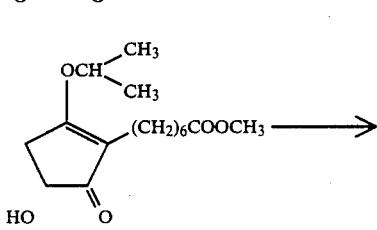

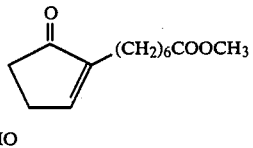

(3) Acta Chimica Academiae Scientiarum Hungariae, Tomus 102(1), pp. 91–100 (1979)

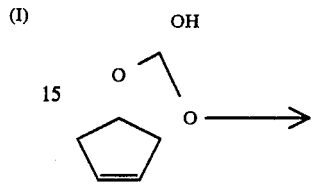

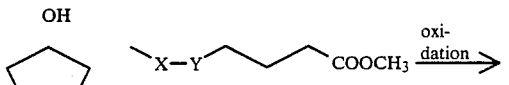

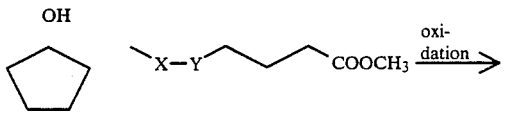

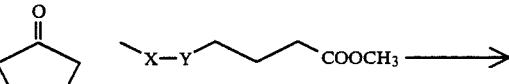

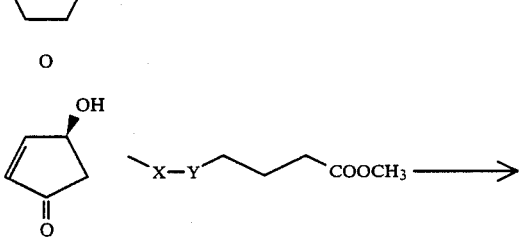

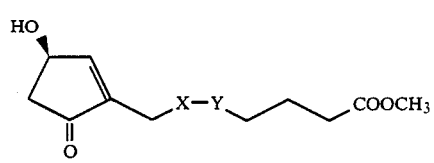

These conventional processes are, however, disadvantageous from the practical viewpoint. For instance, the objective compound in process (1) is not satisfactory with regard to its yield and optical purity. In addition, said process inevitably produces several kinds of by-products. Process (2) requires the use of a triketone, which is not readily available, as the starting material and many steps for its conversion into the objective compound. In Process (3), the starting (−)-cis-2-oxobicyclo[3.3.0]-oct-6-en-3-ol is required to be in an optically active form and the conversion into the objective compound is accomplished only through a number of troublesome steps.

As the result of an extensive study for realization of an industrially advantageous process for production of the cyclopentenone (I) in a good yield, with a high purity and at a low production cost, it has now been found that the cyclopentenone (I) is obtainable from the corresponding dl-cyclopentenone ester of the formula:

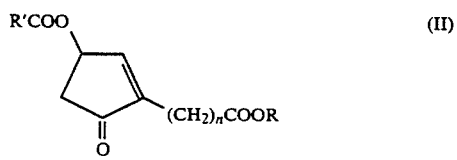

wherein R and n are each as defined above and R' is a lower alkyl group optionally substituted with halogen in a single step, i.e. by subjecting the dl-cyclopentenone ester (II) to asymmetric hydrolysis with an enzyme capable of hydrolyzing selectively either one of the d- or l-form isomer in the dl-cyclopentenone ester (II).

The asymmetric hydrolysis is accomplished by treating the starting dl-cyclopentenone ester (II) with an enzyme so as to hydrolyze either one of the optically active isomers, i.e. the d- or l-form in the dl-cyclopentenone ester (II). As the enzyme, there may be used any esterase which can hydrolyze selectively either one of the optically active isomers (i.e. the d- or l-form) in the dl-cyclopentenone ester (II). Such esterase is usually produced by microorganisms or obtainable from animals and plants. Yet, the term "esterase" used in this specification is to be construed broadly so as to cover "lipase" as well.

The microorganism which can produce the esterase may be chosen from Enterobacter, Arthrobacter, Brevibacterium, Pseudomonas, Alcaligenes, Micrococcus, Chromobacterium, Microbacterium, Corynebacterium, Bacillus, Lactobacillus, Trichoderma, Candida, Saccharomyces, Rhodotorula, Cryptococcus, Tcrulopsis, Pychia, Penicillium, Aspergillus, Rhizopus, Mucor, Aureovacidium, Actynomucor, Nocardia, Streptomyces, Hansenula, Achromobacter, etc. Production of the esterase may be effected by cultivating said microorganism in a culture medium by a per se conventional procedure. For instance, the microorganism is inoculated in a sterilized liquid medium, which is then subjected to reciprocal shaking at a temperature of 20° to 40° C. for a period of 1 to 3 days. In case of the microorganism being chosen from fungi or yeasts, the culture medium may comprise, for instance, peptone (5 g), glucose (10 g), malt extract (3 g) and yeast extract (3 g) per 1,000 ml of water (pH 6.5) (maltose extract-yeast extract medium). In case of the microorganism being chosen from bacteria, the culture medium may comprise, for instance, glucose (10 g), peptone (5 g), meat extract (5 g) and NaCl (3 g) per 1,000 ml of water (pH 7.2) (saccharide-added bouillon medium).

Some microorganism-originated esterases are available on the market. Examples of such commercially available esterases as usable in this invention are lipase produced by Pseudomonas ("Lipase P"; Amano Pharmaceutical Co., Ltd.), lipase produced by Aspergillus ("Lipase AP"; Amano Pharmaceutical Co., Ltd.), lipase produced by Mucor ("Lipase M-AP"; Amano Pharmaceutical Co., Ltd.), lipase produced by Candida cylindracea ("Lipase MY"; Meito Sangyo Co., Ltd.), lipase produced by Alcaligenes ("Lipase PL"; Meito Sangyo Co., Ltd.), lipase produced by Achromobacter ("Lipase AL"; Meito Sangyo Co., Ltd.), lipase produced Arthrobacter (Shin-Nippon Chemical Co., Ltd.), lipase produced by Chromobacterium (Toyojozo Co., Ltd.), lipase produced by Rhizopus delemar ("Talipase"; Tanabe Seiyaku Co., Ltd.), lipase produced by Rhizopus ("Lipase Saiken"; Osaka Saikin Kenkyuso), etc.

Examples of the esterase obtainable from animals or plants and usable in this invention are steapsin, pancreatin, pig liver esterase, wheat germ esterase, etc.

In the process of the invention, the esterase may be employed in any conventional form such as a purified form, a crude form, a mixture with other enzymes, a fermentation broth, a microbial body, a fermentation broth filtrate, etc. Further, the esterase as separated and the microorganism capable of producing the esterase may be used alone or in combination. Furthermore, the esterase or the microorganism having a capability of producing the esterase may be used in any immobilized form, e.g. in a form fixed on resinous particles.

The asymmetric hydrolysis is normally performed by contacting the dl -cyclopentenone ester (II) with the esterase itself or the microorganism capable of producing the same in a buffer under vigorous agitation. As the buffer, there may be used the one comprising an inorganic salt(s) such as sodium phosphate or potassium phosphate and/or an organic salt(s) such as sodium acetate or sodium citrate. When an alkali-philic microorganism or an alkaline esterase is used, the buffer is preferred to be kept at a pH of 8 to 11. When the microorganism is not alkali-philic or the esterase is not resistant to alkali, the pH of the buffer is favored to be from about 5 to 8. The concentration of the buffer may be usually from about 0.05 to 2M, preferably from about 0.05 to 0.5M. The reaction temperature is normally from about 10° to 60° C., and the reaction time is generally from about 4 to 70 hours.

As the result of the asymmetric hydrolysis, either one of the d- or l-form isomer in the dl-cyclopentenone ester (II) is selectively hydrolyzed to give the optically active cyclopentenone (I) while leaving the other isomer in the starting dl-cyclopentenone ester (II). Thus, the reaction mixture comprises &:he optically active cyclopentenone (I) as the hydrolyzed product and the optically active cyclopentenone ester as the non-hydrolyzed product.

For recovery of those optically active compounds from the reaction mixture, the reaction mixture may be, for instance, extracted with an appropriate solvent (e.g. methylisobutylketone, ethyl acetate, diethyl ether). After removal of the solvent from the extract, the residue is subjected to further separation or purification such as distillation, column chromatography or recrystallization to collect the optically active cyclopentenone (I) and the ester of the optically active cyclopentenone (I) as an enantiomer of the former separately. When desired, the optically active cyclopentenone ester may be then converted into the corresponding optically active cyclopentenone by hydrolysis.

Still, it may be noted that the asymmetric hydrolysis with a lipase produced by a microorganism belonging to Pseudomonas or Arthrobacter can generally afford the optically active cyclopentenone (I) with a fairly high purity. Further, the use of any organic solvent (e.g. toluene, chloroform, methylisobutylketone, dichloromethane) inert to the hydrolytic reaction in addition to the buffer is frequently advantageous, because the asymmetric hydrolysis is accomplished efficiently.

The dl-cyclopentenone ester (II) as the starting material in the process of this invention is obtainable by reacting a hydroxycyclopentenone of the formula:

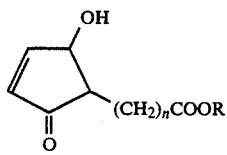

(III)

wherein R and n are each as defined above with an acylating agent to accomplish acylation and rearrangement simultaneously.

The acylating agent usable in this invention comprises three kinds of compounds, i.e. (a) a lower fatty acid such as a lower alkanoic acid (e.g. acetic acid, propionic acid, butyric acid, valeric acid) or a halo(-lower)alkanoic acid (e.g. chloroacetic acid, dichloroacetic acid), (b) a lower fatty acid anhydride such as a lower alkanoic acid anhydride (e.g. acetic anhydride, propionic anhydride, butyric anhydride, valeric anhydride) and (c) a lower fatty acid metal salt such as a lower alkanoic acid metal salt (e.g. lithium acetate, sodium acetate, sodium propionate, sodium butyrate, potassium acetate, potassium propionate, calcium acetate, calcium propionate, copper acetate, zinc acetate, palladium acetate, lead acetate, tin acetate, manganese acetate, cobalt acetate), etc. The lower fatty acid or its anhydride may be used in an amount of about one equivalent or more to the starting hydroxycyclopentenone (III). The lower fatty acid metal salt may be employed in an amount of about 0.01 to 5 equivalent, preferably of about 0.01 to 0.5 equivalent to the hydroxycyclopentenone (III). The presence of the above three components as the acylating agent in the reaction system is quite important, because otherwise the cyclopentenone ester (II) will not be obtainable in an efficient yield.

The reaction is usually carried out in an inert solvent such as a hydrocarbon, a halogenated hydrocarbon, an ether, a ketone, an amide or a sulfoxide. Specific examples of the solvent are hexane, benzene, toluene, chloroform, carbon tetrachloride, dichloromethane, dichloroethane, chlorobenzene, tetrahydrofuran, ethyl ether, acetone, methylethylketone, dimethylformamide, dimethylsulfoxide, etc. These may be employed solely or in combination. No particular limitation is present on the amount of the solvent. The lower fatty acid may be used as such as a reaction medium when it is in a liquid state. The reaction is normally effected at a temperature of about 0° to 150° C., preferably of about 30° to 140° C. The reaction time is not limitative, but an unnecessarily long time is not favorable, because the once produced dl-cyclopentenone ester (II) may be partly decomposed. In general, it is between about 0.5 and 10 hours.

For carrying out the reaction, all of the reactants, i.e. the hydroxycyclopentenone (III) as well as the lower fatty acid, the lower fatty acid anhydride and the lower fatty acid metal salt, may be charged into a reactor, followed by proceeding of the reaction. Alternatively, the hydroxycyclopentenone (III) as well as the lower fatty acid and the lower fatty acid anhydride may be charged in a reactor, followed by proceeding of the reaction for a certain period of time (e.g. about 0.1 to 5 hours); then, the lower fatty acid metal salt is added thereto, followed by further proceeding of the reaction.

The hydroxycyclopentenone (III) as the starting compound in the above process can be prepared by rearrangement of a furan-carbinol of the formula:

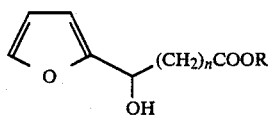

(V)

wherein R and n are each as defined above in an aqueous medium in the presence or absence of a catalyst at a pH of about 3.5 to 6.

The reaction medium may comprise water or its mixture with any inert organic solvent in a small amount. In other words, the reaction medium comprises always water as the major component. The organic solvent which may be optionally contained in a small proportion in the reaction medium is chosen usually from hydrocarbons, alcohols, fatty acids, ethers, esters, etc. Specific examples are ethylene glycol, 1,3-propanediol, methanol, ethanol, dioxane, tetrahydrofuran, dimethylformamide, dimelthylsulfoxide, ethyl acetate, acetic acid, dichlcromethane, toluene, dimethyl ether, etc. Usually, however, the sole use of water is sufficient.

In the reaction, the catalyst is not necessarily required to use, but its use is usually preferred for acceleration of the reaction. The catalyst may be chosen from metal salts, organic quarternary ammonium salts, surfactants, alcohols, etc. Examples of the metal salts are phosphates, sulfates, chlorides, bromides, oxygenated salts, fatty acid salts, sulfonic acid salts, etc. of sodium, potassium, magnesium, zinc, iron, calcium, manganese, cobalt, aluminum, etc. Examples of the organic quarternary ammonium salts are tetrabutylammonium bromide, benzyl trimethylammonium chloride, tricapryl methylammonium chloride, dodecyl trimethylamonium chloride, capryl benzyl dimethylammonium chloride, etc. Examples of the surfactants are higher fatty acid salts, polyoxyethylene alkylphenol ether, higher fatty acid alcohols, etc. Examples of the alcohols are methanol, ethanol, ethylene glycol, etc. These may be used solely or in combination. The amount of the catalyst is normally within a range of about 1/200-5 parts by weight to one part by weight of the starting furan-carbinol, but this is not critical. The catalyst once used in the reaction may be recovered from the reaction mixture and subjected to re-use.

The reaction medium is favorable to have a pH within a range of about 3.5 to 6, especially of about 3.5 to 5.5. In order to keep this pH value, any suitable acidic or basic substance may be added to the reaction mixture. Examples of the acidic substance are inorganic or organic acids such as hydrochloric acid, sulfuric acid, phosphoric acid, boric acid, acetic acid, propionic acid, toluene-sulfonic acid and methanesulfonic acid. Examples of the basic substance are inorganic or organic bases such as sodium hydroxide, potassium carbonate, sodium hydrogen carbonate, potassium hydrogen phosphate, organic amines, etc. Alternatively, a buffer comprising an acidic substance and a basic substance in combination may be used for adjustment of the pH value. Examples of such buffer are potassium hydrogen phosphate-phosphoric acid, sodium acetate-acetic acid, sodium acetate-phosphoric acid, phthalic acid- potassium carbonate, potassium hydrogen phosphate-hydrochloric acid, potassium dihydrogen phosphate potassium hydrogen carbonate, succinic acid-sodium hydrogen carbonate, etc. Usually, the use of a strong acid or base (e.g. hydrochloric acid, hydrobromic acid, sodium hydroxide, potassium hydroxide) is to be avoided for adjustment of the pH value.

The reaction temperature may be within a range of about 0° to 200° C., preferably of about 20° to 160° C.

As the result of the above rearrangement, there is produced the hydroxycyclopentenone (III), usually together with a cyclopentenone compound of the formula:

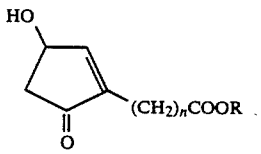 (IV)

wherein R and n are each as defined above.

The thus produced hydroxycyclopentenone (III) may be used as the starting compound for production of the dl-cyclopentenone ester (II) with or without its previous separation from its mixture with the cyclopentenone compound (IV). From the industrial viewpoint, the use of a mixture of the hydroxycyclopentenone (III) and the cyclopentenone compound (IV) without their separation is favorable, because only acylation proceeds on the cyclopentenone compound (IV) to give the dl-cyclopentenone ester (II) when reacted with the acylating agent as above.

In the procedure as stated above, acylation and isomerization proceeds simultaneously on the hydroxycyclopentenone (III) to give the dl-cyclopentenone ester (II). In place of said procedure, the hydroxycyclopentenone (III) may be first isomerized to the cyclopentenone compound (IV), which is then acylated to the dl-cyclopentenone ester (II), although said procedure comprising simultaneous proceeding of acylation and isomerization is more favorable from the viewpoints of the simplicity of the reaction operation, the yield of the product and so on.

In the isomerization, the hydroxycyclopentenone (III) may be used in the form of a mixture with the cyclopentenone compound (IV) or in a pure form after separation from such mixture. From the industrial viewpoint, the use of the hydroxycyclopentenone (III) in the mixture form is advantageous, because the cyclopentenone compound (IV) is inert to the reaction in the isomerization while it is the objective compound in the isomerization. The isomerization may be carried out by treatment of the hydroxycyclopentenone (III) in an inert solvent in the presence or absence of a catalyst at a pH of 6 to 9. As the inert solvent, there may be exemplified water or its mixture with an organic solvent in a small amount. Examples of the organic solvent are alcohols (e.g. ethylene glycol, 1,3-propanediol, methanol, ethanol), ethers (e.g. dimethyl ether, dioxane, tetrahydrofuran), amides (e.g. dimethylformamide), sulfoxides (e.g. dimethylsulfoxide), esters (e.g. ethyl acetate), acids (e.g. acetic acid), hydrocarbons (e.g. benzene, toluene), halogenated hydrocarbons (e.g. dichloromethane, chloroform), etc. However, any advantage is usually not seen in incorporating such organic solvent into water. The catalyst is not necessarily required to use, but its use is usually favorable for promotion of the reaction rate. The catalyst may be chosen from metal salts, organic quarternary ammonium salts, surfactants, alcohols, etc. Examples of the metal salts are phosphates, sulfates, chlorides, bromides, oxygenated salts, fatty acid salts, sulfonic acid salts, etc. of sodium, potassium, magnesium, zinc, iron, calcium, manganese, cobalt, aluminum, etc. Examples of the organic quarternary ammonium salts are tetrabutylammonium bromide, benzyl trimethylammonium chloride, tricapryl methylammonium chloride, dodecyl trimethylammonium chloride, capryl benzyl dimethylammonium chloride, etc. Examples of the surfactants are higher fatty acid salts, polyoxyethylene alkylphenol ether, higher fatty acid alcohols, etc. Examples of the alcohols are methanol, ethanol, ethylene glycol, etc. These may be used solely or in combination. The amount of the catalyst is normally within a range of about 1/200–5 parts by weight to one part by weight of the starting hydroxycyclopentenone, but this is not critical.

The reaction medium is favorable to have a pH within a range of about 6 to 9, especially of about 7 to 9. In order to keep this pH value, any suitable acidic or basic substance may be added to the reaction mixture. Examples of the acidic substance are inorganic or organic acids such as hydrochloric acid, sulfuric acid, phosphoric acid, boric acid, acetic acid, propionic acid, toluenesulfonic acid and methanesulfonic acid. Examples of the basic substance are inorganic or organic bases such as sodium hydroxide, potassium carbonate, sodium hydrogen carbonate, potassium hydrogen phosphate, organic amines, etc. Alternatively, a buffer comprising an acidic substance and a basic substance in combination may be used for adjustment of the pH value. Examples of such buffer are potassium hydrogen phosphate-phosphoric acid, sodium acetate-acetic acid, sodium acetate-phosphoric acid, phthalic acid-potassium carbonate, potassium hydrogen phosphate-hydrochloric acid, potassium dihydrogen phosphate-potassium hydrogen carbonate, succinic acid-sodium hydrogen carbonate, etc. It is usually preferred to avoid the use of a strong acid or base (e.g. hydrochloric acid, hydrobromic acid, sodium hydroxide, potassium hydroxide) for adjustment of the pH value.

The reaction temperature may be within a range of about 0° to 200° C., preferably of about 20° to 160° C.

After completion of the reaction, the reaction mixture may be subjected to per se conventional separation or purification treatment such as extraction, concentration, distillation, chromatography or recrystallization to obtain the cyclopentenone compound (IV).

The isomerization may be also carried out by treating the hydroxycyclopentenone (III) in the presence of chloral and an organic amine in an inert solvent. In this treatment, chloral is normally used in an amount of about 0.005 to 1 mol, preferably of about 0.01 to 0.3 mol, to one mole of the hydroxycyclopentenone (III). The use of an organic amine is industrially advantageous, because it can reduce the amount of chloral. As the organic amine, the use of a tertiary amine (e.g. triethylamine, N-methylmorpholine, N-methylpiperazine, N,N'-dimethylpiperazine, pyridine, lutidine) is favored. Usually, the organic amine is employed in an amount of about 0.005 to 0.4 mol to one mol of the hydroxycyclopentenone (III). Examples of the inert solvent are ethers (e.g. tetrahydrofuran, dioxane), ketones (e.g. acetone), hydrocarbons (e.g. heptane, cyclohexane, benzene, toluene), halogenated hydrocarbons (e.g. chlorobenzene, dichloromethane, dichloroethane), esters (e.g. ethyl acetate), etc. The reaction temperature may be within a range of about −10° to 100° C., preferably of about 0° to 90° C.

After completion of the reaction, the reaction mixture may be subjected to per se conventional separation or purification treatment such as extraction, concentration, distillation, chromatography or recrystallization to obtain the cyclopentenone compound (IV).

The acylation of the cyclopentenone compound (IV) to the dl-cyclopentenone ester (II) may be performed by a per se conventional acylation procedure. For instance, the cyclopentenone compound (IV) is reacted with a lower fatty acid in a reactive form, if necessary, in the presence of any reaction aid in an inert solvent to give the dl-cyclopentenone ester (II). As the reactive form of the lower fatty acid, there are exemplified a lower fatty acid halide such as a lower alkanoyl halide (e.g. acetyl chloride, acetyl bromide, propionyl chloride, propionyl bromide, butyryl chloride, butyryl bromide) or a halogenated lower alkanoic acid talide (e.g. chloroacetyl chloride, chloroacetyl bromide, dichloroacetyl chloride, dichloroacetyl bromide), a lower fatty acid anhydride such as a lower alkanoic anhydride (e.g. acetic anhydride, propionic anhydride), etc. Usually, the lower fatty acid in a reactive form may be used in an amount of about one equivalent or more, particularly of about 1 to 4 equivalents, to the cyclopentenone compound (IV). When an inert solvent is used in the reaction, such inert solvent may be chosen from ethers (e.g. tetrahydrofuran, diethyl ether), ketones (e.g. acetone, methylethylketone), hydrocarbons (e.g. hexane, toluene, benzene), halogenated hydrocarbons (e.g. chlorobenzene, dichloromethane, dichloroethane, chloroform, carbon tetrachloride), amides (e.g. dimethylformamide), etc. As the reaction aid, there is advantageously used an organic or inorganic basic substance (e.g. triethylamine, tri-n-butylamine, pyridine, picoline, sodium carbonate, sodium methoxide, potassium hydrogen carbonate) in an amount of about 1 to 5 equivalents to the cyclopentenone compound (IV) in order to effect the reaction smoothly and promptly. When an organic amine is used as a reaction medium, it may simultaneously serve as the reaction aid. An acidic substance such as toluenesulfonic acid, methanesulfonic acid or sulfuric acid is also usable as the reaction aid.

The reaction temperature is usually within a range of about $-20°$ to $150°$ C., preferably of about $-10°$ to $120°$ C. Any particular limitation is not present on the reaction time.

After completion of the reaction, the reaction mixture may be post-treated according to a per se conventional separation or purification procedure such as extraction, separation, concentration or distillation to give the dl-cyclopentenone ester (II).

Practical and presently preferred embodiments of the invention are illustratively shown in the following Examples.

EXAMPLE 1

(1) Into a four necked-flask equipped with a stirrer and a thermometer, 2-(1-hydroxy-7-methoxycarbonyl-heptyl)-furan 114 g), water (4560 g) and potassium monohydrogen phosphate-phosphoric acid buffer (3.8 g) were charged, and the resulting mixture (pH 4.2) was stirred at 100° C. under nitrogen stream until the starting compound was consumed perfectly. The reaction mixture was cooled and extracted with methylisobutyl-ketone (600 ml) two times. The extracts were combined together and concentrated under reduced pressure to give a mixture (92 g) of 3-hydroxy-2-(6-methoxycarbonylhexyl)-4-cyclopentenone and 4-hydroxy-2-(6-methoxycarbonylhexyl)-2-cyclopentenone. Yield, 80.7%.

(2) The above obtained mixture (12.0 g) was combined with acetic acid (17.0 g), acetic anhydride (5.1 g) and anhydrous sodium acetate (0.29 g), and the resultant mixture was heated at 120° C. for 4 hours. After termination of the reaction was confirmed by gas chromatography, the reaction mixture was concentrated under reduced pressure. To the concentrated residue, toluene (200 ml) and water (100 ml) were added thereto, followed by shaking. The organic layer was separated, washed with 3% sodium bicarbonate solution and water in order, dried over anhydrous magnesium sulfate and concentrated to give 4-acetoxy-2-(6-methoxycarbonyl-hexyl)-2-cyclopentenone (13.1 g). Yield, 93%. b.p., 180°–185° C./0.6 mmHg.

(3) 4-Acetoxy-2-(6-methoxycarbonylhexyl)-2-cyclopentenone (4 g), dichloromethane (2 ml) and a lipase (400 mg) produced by a microorganism belonging to Pseudomonas ("Amano Lipase P" manufactured by Amano Pharmaceutical Co., Ltd.) were charged into a flask, and the resulting mixture was stirred vigorously at 25° to 30° C. for 13 hours. After completion of the reaction, the reaction mixture was extracted with toluene (40 ml) two times. The extracts were combined together and concentrated under reduced pressure to give a residue (3.98 g), which was subjected to column chromatography using a mixture of toluene and ethyl acetate (5:3) as an eluting solvent to give 4R(+)-hydroxy-2-(6-methoxycarbonylhexyl)- 2-cyclo-pentenone (1.01 g) ($[\alpha]_D^{20}+15.1°$ (c=1, methanol) (88% ee); m.p., 58° C.) and 4S(−)-acetoxy-2-(6-methoxycarbonylhexyl)-2-cyclopentenone (2.60 g) ($[\alpha]_D^{20}-43.1°$ (c=1, methanol); m.p., 41° C.).

(4) 4-Acetoxy-2-(6-methoxycarbonylhexyl)-2-cyclopentenone (4 g) and a lipase (400 mg) produced by a microorganism belonging to Pseudomonas ("Amano Lipase P" manufactured by Amano Pharmaceutical Co., Ltd.) were charged into a flask, and the resulting mixture was stirred vigorously at 40° C. for 5 hours. After completion of the reaction, the reaction mixture was treated in the same manner as in Example 1 (3) to give 4R(+)-hydroxy-2-(6-methoxycarbonylhexyl)-2-cyclopentenone (0.98 g) ($[\alpha]_D^{20}14.9°$ (c=1, methanol) (86.7% ee)) and 4S(−)-acetoxy-2-(6-methoxycarbonylhexyl)-2-cyclopentenone (2.66 g) ($[\alpha]_D^{20}43.5°$ (c=1, methanol)).

EXAMPLE 2

(1) Into the same flask as in Example 1, a mixture of 3-hydroxy-2-(6-methoxycarbonylhexyl)-4-cyclopentenone and 4-hydroxy-2-(6-methoxycarbonylhexyl)-2-cyclopentenone (weight proportion, 3:1) (72.0 g; 0.3 mol), water (2200 g) and acetic acid-1N sodium hydroxide buffer (2.4 g) were charged, and the resulting mixture (pH 8) was stirred at 100° C. under nitrogen stream until the starting compound was consumed perfectly. After completion of the reaction, the reaction mixture was cooled and extracted with methylisobutylketone (600 g) two times. The extracts were combined together and concentrated under reduced pressure to give 4-hydroxy-2-(6-methoxycarbonylhexyl)-2-cyclopentenone (60 g). Yield, 83.2%. $n_D^{25}=1.4875$.

(2) A mixture of 3-hydroxy-2-(6-methoxycarbonyl-hexyl)-4-cyclopentenone and 4-hydroxy-2-(6-methoxycarbonylhexyl)-2-cyclopentenone (weight proportion, 3:1) (5 g), chloral (0.46 g), pyridine (0.29 g) and toluene (20 ml) were charged in a reactor and stirred at 30° to 40° C. for 6 hours. After completion of the reaction, the reaction mixture was washed with water, 1% hydrochloric acid, 1% sodium bicarbonate solution and water in order. The organic layer was concentrated to give 4-hydroxy-2-(6-methoxycarbonylhexyl)-2-cyclopentenone (4.9 g). Yield, 98%.

(3) 4-Hydroxy-2-(6-methoxycarbonylhexyl)-2-cyclopentenone (24 g) was dissolved in chloroform (200 ml), followed by addition of acetyl chloride (7.9 g) thereto. Triethylamine [10.1 g] was dropwise added thereto while stirring at 0° to 10° C. After completion of the addition, stirring was continued at 25° C. for 8 hours. The reaction mixture was washed with water, dried over anhydrous magnesium sulfate and concentrated under reduced pressure to give 4-acetoxy-2-(6-methoxycarbonylhexyl)-2-cyclopentenone (27.6 g). Yield, 98%.

(4) 4-Acetoxy-2-(6-methoxycarbonylhexyl)-2-cyclopentenone (4 g), dichloromethane (2 ml) and a lipase (300 mg) produced by a microorganism belonging to Arthrobacter (manufactured by Sin-Nippon Chemical Co., Ltd.) were charged into a reactor. Asymmetric hydrolysis was carried out in the same manner as in Example 1 (3), followed by post-treatment to give 4R(+)-hydroxy-2-(6-methoxycarbonylhexyl)-2-cyclopentenone (1.21 g) ($[\alpha]_D^{20}+16.1°$ (c=1, methanol) (94.8% ee)) and 4S(−)-acetoxy-2-(6-methoxycarbonylhexyl)-2-cyclopentenone (2.54 g) ($[\alpha]_D^{20}-40.4°$ (c=1, methanol)).

(5) 4-Acetoxy-2-(6-methoxycarbonylhexyl)-2-cyclopentenone (4 g) and a lipase (300 mg) produced by a microorganism belonging to Arthrobacter (manufactured by Sin-Nippon Chemical Co., Ltd.) were charged into a reactor, and the resulting mixture was treated in the same manner as in Example 1 (4) for asymmetric hydrolysis, followed by post-treatment to give 4R(+)-hydroxy-2-(6-methoxycarbonylhexyl)-2-cyclopentenone ($[\alpha]_D^{20}+15.8°$ (c=1, methanol) (92.3% ee)) and 4S(−)-acetoxy-2-(6-methoxycarbonylhexyl)-2-cyclopentenone ($[\alpha]_D^{20}-42°$ (c=1, methanol)).

EXAMPLE 3

In the same manner as in Example 2 (1) but using a mixture of 3-hydroxy-2-(4-methoxycarbonylbutyl)-4-cyclopentenone and 4-hydroxy-2-(4-methoxycarbonylbutyl)-2-cyclopentenone (weight proportion, 3:1) (0.25 mol; 52.5 g), there was produced 4-hydroxy-2-(4-methoxycarbonylbutyl)-2-cyclopentenone (42.1 g). Yield, 80.2%.

The thus obtained 4-hydroxy-2-(4-methoxycarbonylbutyl)-2-cyclopetenone was subjected to asymmetric hydrolysis in the same manner as in Example 2 (3) or 2 (4) to give 4R(+)-hydroxy-2-(4-methoxycarbonylbutyl)-2-cyclopentenone.

EXAMPLE 4

Into the same flask as in Example 1, 2-(1-hydroxy-7-ethoxycarbonylheptyl)-furan (18 g) and water (720 g) were charged, and the resultant mixture (pH, 4.2–4.5) was stirred at 100° C. until the starting compound was consumed completely. After completion of the reaction, the reaction mixture was post-treated in the same manner as in Example 1 (1) to give a mixture of 3-hydroxy-2-(6-ethoxycarbonylhexyl)-4-cyclopentenone and 4-hydroxy-2-(6-ethoxycarbonylhexyl)-2-cyclopentenone (14.4 g). Yield, 79.8%.

To the mixture (12.7 g) as above obtained, sodium acetate (2.1 g), acetic anhydride (5.1 g) and acetic acid (40 g), and the resultant mixture was heated at 110° C. for 4 hours. After completion of the reaction, the reaction mixture was treated in the same manner as in Example 1 (2) to give 4-acetoxy-2-(6-ethoxycarbonylhexyl)-2-cyclopentenone (14.9 g). Yield, 95.1%. b.p., 189°–193° C./0.5 mmHg.

The thus obtained 4-acetoxy-2-(6-ethoxycarbonylhexyl)-2-cyclopetenone was subjected to asymmetric hydrolysis in the same manner as in Example 1 (3) to give 4R(+)-hydroxy-2-(6-ethoxycarbonylhexyl)-2-cyclopentenone.

What is claimed is:

1. A process for preparing an optically active cyclopentenone of the formula:

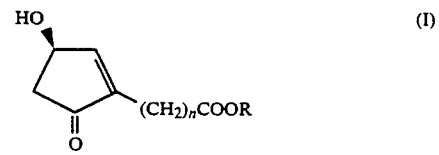

wherein R is a hydrogen atom or a lower alkyl group and n is an integer of 4 to 8, which comprises contacting a di-cyclopentenone ester of the formula:

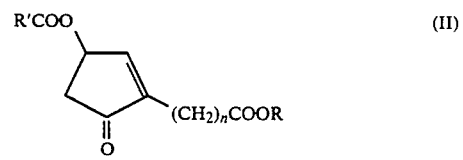

wherein R and n are each as defined above and R, is a lower alkyl group, or a lower alkyl group substituted with halogen, with an enzyme having a capability of hydrolyzing selectively either one of the d- or l-form isomers of the dl-cyclopentenone ester (ii) in an aqueous medium for asymmetric hydrolysis.

2. The process according to claim 1, wherein the enzyme is produced by a microorganism chosen from Pseudomonas, Aspergiluus, Mucor, Candida cylindracea, Alcaligenes, Achromobacter, Arthrobacter, Chromobacterium or Rhizopus delemar.

3. The process according to claim 1, wherein the aqueous medium comprises a buffer.

4. The process according to claim 3, wherein the aqueous medium includes an organic solvent.

5. The process according to claim 1, wherein the contact is carried out under stirring.

6. The process according to claim 5, wherein the contact is carried out at a temperature of about 10° to 60° C.

7. A process for preparing an optically active cyclopentenone of the formula:

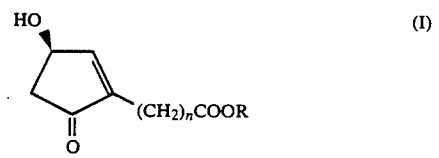

wherein R is a hydrogen atom or a lower alkyl group and n is an integer of 4 to 8, which comprises the following steps:

Step (1) reacting a hydroxycyclopentenone of the formula:

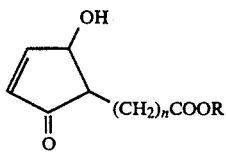 (III)

wherein R is a hydrogen atom or a lower alkyl group and n is an integer of 4 to 8, with an acylating agent comprising a $C_2$-$C_5$ lower fatty acid, a $C_2$-$C_5$ lower fatty acid anhydride or a $C_2$-$C_5$ lower fatty acid metal salt, to give a dl-cyclopentenone ester of the formula:

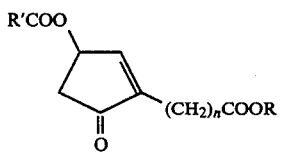 (II)

wherein R and n are each as defined above and $R_1$ is a lower alkyl group, or a lower alkyl group substituted with halogen; and Step (2) contacting the compound of formula (II) with an enzyme having a capability of hydrolyzing selectively either one of the d- or l-form isomers of the dl-cyclopentenone ester (II) in an aqueous medium for asymmetric hydrolysis, to give the compound of formula (I).

8. The process according to claim 7, wherein the lower fatty acid is a $C_2$-$C_5$ lower alkanoic acid, the lower fatty acid anhydride is a $C_2$-$C_5$ lower alkanoic anhydride and the lower fatty acid metal salt is a metal salt of a $C_2$-$C_5$ lower alkanoic acid.

9. The process according to claim 8, wherein the lower fatty acid is acetic acid, propionic acid, butyric acid or valeric acid.

10. The process according to claim 8, wherein the lower fatty acid metal salt is the lithium salt, sodium salt, potassium salt, calcium salt, copper salt, zinc salt, palladium salt, lead salt, tin salt, manganese salt or cobalt salt of the lower fatty acid.

11. The process according to claim 7, wherein the lower fatty acid and the lower fatty acid anhydride are respectively present in amounts of not less than about one mole per one mole of the dl-cyclopentenone ester (II) and the lower fatty acid metal salt is present in an amount of from about 0.01 to 5 moles per one mole of the dl-cyclopentenone ester (II).

12. The process according to claim 7, wherein Step 1 the reaction is effected at a temperature of about 30° to 140° C.

13. A process for preparing an optically active cyclopentenone of the formula:

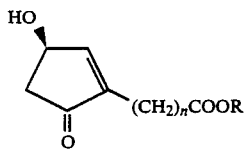 (I)

wherein R is a hydrogen atom or a lower alkyl group an n is an integer of 4 to 8, which comprises the following steps:

Step (1) reacting a cyclopentenone compound of the formula:

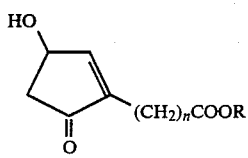 (IV)

wherein R and n are each as defined above, with a $C_2$-$C_5$ lower fatty acid anhydride or halide, to give a dl-cyclopetenone ester of the formula:

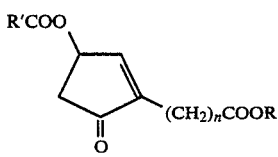 (II)

wherein R and n are each as defined above and $R_1$ is a lower alkyl group, or a lower alkyl group substituted with halogen; and Step (2) contacting the compound of formula (II) with an enzyme having a capability of hydrolyzing selectively either one of the d- or l-form isomers of the dl-cyclopentenone ester (ii) in an aqueous medium for asymmetric hydrolysis, to give the compound of formula (I).

14. The process according to claim 13; wherein the lower fatty acid anhydride is acetic anhydride, propionic anhydride, butyric anhydride, valeric anhydride, chloroacetic anhydride or dichloroacetic anhydride.

15. The process according to claim 13, wherein the lower fatty acid halide is acetyl chloride, acetyl bromide, propionyl chloride, propionyl bromide, butyryl chloride, butyryl bromide, chloroactyl chloride, chloroacetyl bromide, dichloroacetyl chloride or dichloroacetyl bromide.

16. The process according to claim 13, wherein the lower fatty acid anhydride or halide is present in an amount of about 1 to 4 moles per one mole of the cyclopentenone compound (IV).

17. The process according to claim 13, wherein the compound of formula (IV) is reacted in step 1 with a $C_2$-$C_3$ lower fatty acid anhydride or halide, in the presence of either a basic substance or an acidic substance, to give the compound of formula (II).

18. The process according to claim 13, wherein the compound of formula (IV) is reacted in step 1 with a $C_2$-$C_5$ lower fatty acid anhydride or halide, in the presence of a basic substance to give the compound of formula II.

19. The process according to claim 18, wherein the basic substance is triethylamine, tri-n-butylamine, pyridine, picoline, sodium carbonate, sodium methoxide or potassium hydrogen carbonate.

20. The process according to claim 17, wherein the amount of the basic substance or the acidic substance present is from about 1 to 5 moles per one mole of the cyclopentenone compound (IV).

21. The process according to claim 13, wherein the reaction Step 1 is carried out at a temperature of about −10° to 120° C.

22. A process for preparing an optically active cyclopentenone of the formula:

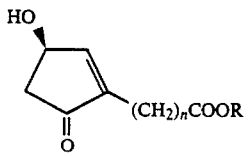
(I)

wherein R is a hydrogen atom or a lower alkyl group and n is an integer of 4 to 8, which comprises the following steps:

Step (1) treating a hydroxycyclopentenone of the formula:

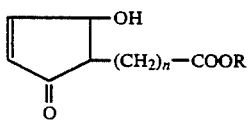
(III)

wherein R and n is each as defined above, in an aqueous medium at a pH of about 6 to 9 to give a compound of the formula:

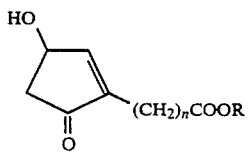
(IV)

wherein R and n are each as defined above;

Step (2) reacting the compound of formula (IV) with a C₂–C₅ lower fatty acid anhydride or halide, to give a dl-cyclopentenone ester of the formula:

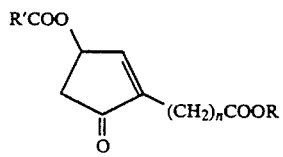
(II)

wherein R and n are each as defined above and R' is a lower alkyl group, or a lower alkyl group substituted with halogen; and Step (3) contacting the compound of formula (II) with an enzyme having a capability of hydrolyzing selectively either one of the d- or l-form isomers of the dl-cyclopentenone ester (II) in an aqueous medium for asymmetric hydrolysis, to give the compound of formula (I).

23. The process according to claim 22, wherein the aqueous medium comprises water at least as a major component.

24. The process according to claim 22, wherein Step 1 is carried out in the presence of a catalyst.

25. The process according to claim 24, wherein the catalyst is chosen from acid metal salts, organic quaternary ammonium salts, surfactants or alcohols.

26. The process according to claim 25, wherein the catalyst is an acid metal salt chosen from sodium, potassium, magnesium, zinc, iron, calcium, manganese, cobalt or aluminum salts of inorganic acids, fatty acids or organic sulfonic acids.

27. The process according to claim 25, wherein the catalyst is an organic quaternary ammonium salt chosen from tetrabutyl ammonium bromide, benzyl trimethyl ammonium chloride, tricapryl methyl ammonium chloride, dodecyl trimethyl ammonium chloride or capryl benzyl dimethyl ammonium chloride.

28. The process according to claim 25, wherein the catalyst is an alcohol chosen from methanol, ethanol or ethylene glycol.

29. The process according to claim 24, wherein the catalyst is used in an amount of about 1/200 to 5 parts by weight to one part by weight of the hydrocyclopentenone (III).

30. The process according to claim 22, wherein the reaction Step 1 is carried out at a temperature of about 20° to 120° C.

31. A process for preparing an optically active cyclopentenone of the formula:

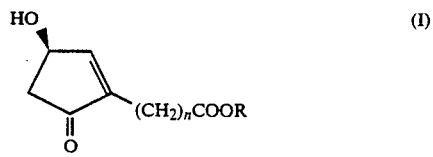
(I)

wherein R is a hydrogen atom or a lower alkyl group and n is an integer of 4 to 8, which comprises the following steps:

Step (1) treating a hydroxycyclopentenone of the formula:

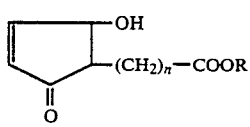

wherein R and n is each as defined above, with chloral and an organic amine in a liquid medium to give a compound of the formula:

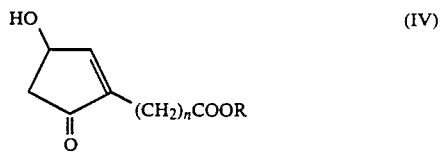
(IV)

wherein R and n are each as defined above:

Step (2) reacting compound (IV) with a C₂–C₅ lower fatty acid anhydride or halide, to give a dl-cyclopentenone ester of the formula:

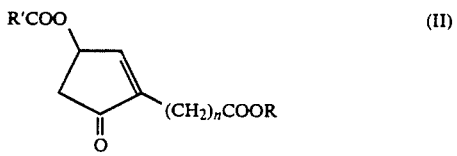
(II)

wherein R and n are each as defined above and R, is a lower alkyl group, or a lower alkyl group substituted with halogen; and Step (3) contacting the compound of formula (II) with an enzyme having a capability of hydrolyzing selectively either one of the d- or l-form isomers of the dl-cyclopentenone ester (II) in an aqueous medium for asymmetric hydrolysis, to give the compound of formula (I).

32. The process according to claim 31, wherein the organic amine is an organic tertiary amine.

33. The process according to claim 32, wherein the organic tertiary amine is chosen from triethylamine, N-methylmorphorine, N-methylpiperazine, N,N'-dimethylpiperazine, pyridine or lutidine.

34. The process according to claim 31, wherein in Step 1 the chloral is used in an amount of about 0.005 to 1 mole per one mole of the hydroxycyclopentenone (III).

35. The process according to claim 31, wherein in Step 1 the organic amine is used in an amount of about 0.005 to 0.4 mole per one mole of the hydroxycyclopentenone (III).

36. The process according to claim 31, wherein in Step 1 the liquid medium is the one chosen from hydrocarbons, halogenated hydrocarbons, ethers, ketones or esters.

37. The process according to claim 31, wherein the reaction Step 1 is carried out at a temperature of about 0° to 90° C.

* * * * *